(12) United States Patent
Benner

(10) Patent No.: US 10,472,383 B2
(45) Date of Patent: Nov. 12, 2019

(54) NUCLEOSIDE TRIPHOSPHATES WITH STABLE AMINOXY GROUPS

(71) Applicant: Steven A Benner, Gainesville, FL (US)

(72) Inventor: Steven A Benner, Gainesville, FL (US)

(*) Notice: Subject to any disclaimer, the term of this patent is extended or adjusted under 35 U.S.C. 154(b) by 11 days.

(21) Appl. No.: 15/460,475

(22) Filed: Mar. 16, 2017

(65) Prior Publication Data

US 2018/0265537 A1    Sep. 20, 2018

(51) Int. Cl.
*C07H 19/04*   (2006.01)
*C07H 19/20*   (2006.01)
*C07H 19/10*   (2006.01)

(52) U.S. Cl.
CPC .............. *C07H 19/10* (2013.01); *C07H 19/20* (2013.01)

(58) Field of Classification Search
None
See application file for complete search history.

(56) References Cited

U.S. PATENT DOCUMENTS

| | | | | |
|---|---|---|---|---|
| 7,544,794 B1* | 6/2009 | Benner | ................ | C07H 19/044 536/27.61 |
| 8,034,923 B1* | 10/2011 | Benner | ................ | C07H 19/10 536/25.1 |
| 8,212,020 B2* | 7/2012 | Benner | ................ | C07H 19/073 536/17.9 |

OTHER PUBLICATIONS

Schoetzau et al. Chem. Commun. (1996), pp. 387-388.*

* cited by examiner

*Primary Examiner* — Patrick T Lewis
(74) *Attorney, Agent, or Firm* — Saliwanchik, Lloyd & Eisenschenk

(57) ABSTRACT

This invention claims aqueous compositions that comprise triphosphates of 2'-deoxynucleoside derivatives that have, instead of a 3'-OH moiety, a 3'-$ONH_2$ moiety; wherein said compositions contain less than 0.5 mole percent contaminating triphosphate having a 3'-OH moiety, as well as processes for providing such compositions. The compositions further must contain insubstantial amounts of hydroxylamine.

15 Claims, 4 Drawing Sheets

NUCLEOSIDE TRIPHOSPHATES WITH STABLE AMINOXY GROUPS

STATEMENT OF RIGHTS TO INVENTIONS MADE UNDER FEDERALLY-SPONSORED RESEARCH

Figure 1:
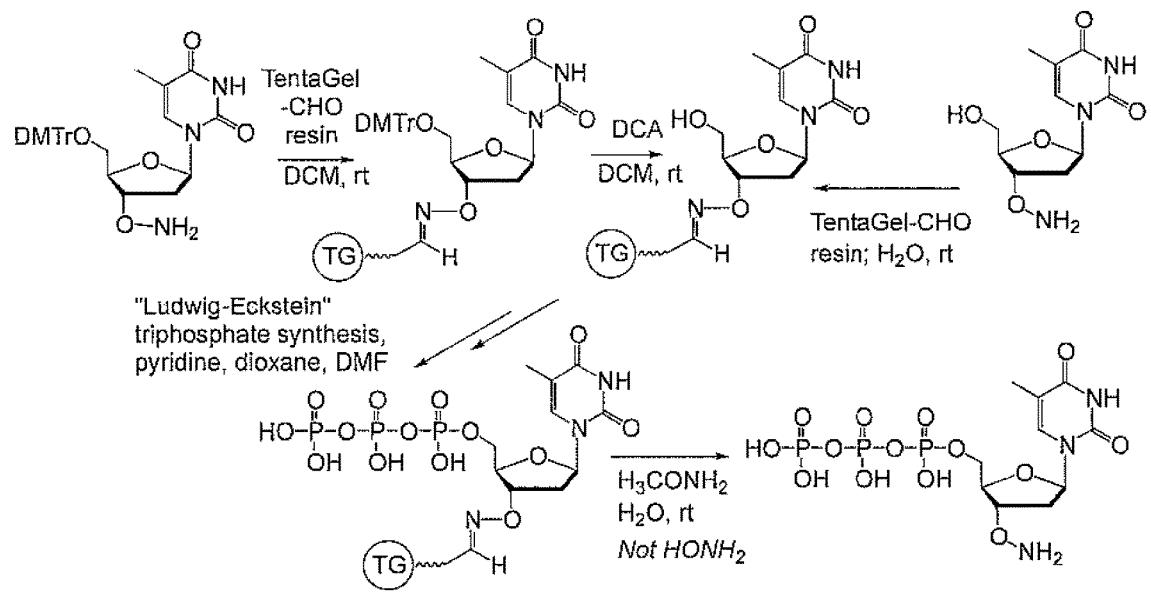

This invention was made with government support under NNX14AK37G, awarded by the National Aeronautics and Space Administration, and under R01GM111386, awarded by the National Institutes of Health. The government has certain rights in the invention.

CROSS REFERENCE TO RELATED APPLICATIONS

None

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

(1) Field of the Invention

This invention relates to the field of nucleic acid analog chemistry, more specifically to analogs of nucleoside triphosphates whose 3'-oxygen atom is covalently bonded to a moiety that does not allow an oligonucleotide having that nucleotide at its 3'-end to be extended further unless that moiety is removed. This moiety is called a "reversible terminator", a phrase also used in the art to refer to the triphosphate and the nucleotide derived from the triphosphate once incorporated at the 3'-end of an oligonucleotide chain. Still more specifically, this invention relates to compositions where the moiety attached to the 3'-triphosphate oxygen is an amino group; in this case, the triphosphate analog is said to carry an "aminoxy" group. Still more specifically this invention relates to processes for synthesizing such triphosphate analogs, and useful compositions that comprise such triphosphates where the analog does not decompose to give a triphosphate with a free 3'-OH group.

(2) Description of Related Art

Well known in the art are processes that require that the enzymatic extension of an oligonucleotide be terminated after introduction of a nucleotide at the 3'-end. This extension can be either untemplated, such as that catalyzed by the enzyme terminal transferase. It may also be templated, such as that catalyzed by a DNA polymerase, an RNA polymerase, or a reverse transcriptase.

Termination of extension following nucleotide addition is frequently achieved by contacting the enzyme to analog of a nucleoside triphosphate where the nucleoside has been altered so as to no longer have a free 3'-hydroxyl group. The 3'-hydroxyl group can be missing entirely in such an analog, replaced by a hydrogen atom, to generate (of example) a 2',3'-dideoxynucleoside triphosphate. In this case, since no convenient method is available to replace the 3'-H by a 3'-OH group on an oligonucleotide, the termination of the oligonucleotide extension process in the presence of such a triphosphate analog is said to be irreversible.

Other nucleoside and oligonucleotide derivatives lacking the standard 3'-OH have functionality that can be converted to a 3'-OH group under conditions that do not damage oligonucleotides. For example, various patents, including U.S. Pat. Nos. 7,544,794, 8,034,923, and 8,212,020, have disclosed that a 3'-O—NH$_2$ group may be used a reversibly terminating moiety. This 3'-O—NH$_2$ group attached to a nucleoside triphosphate terminates further primer extension of an oligonucleotide once that triphosphate is added to its 3'-end.

This terminating 3'-O—NH$_2$ group may not be removed, allowing its reactivity to be used for a variety of purposes. For example, the 3'-modification can react further to create useful molecules, including oximes, which are created by its reaction with an aldehyde or ketone.

However, if the appropriate reagents are added, the nitrogen-oxygen bond of the 3'-O—NH$_2$ group can be cleaved, thereby converting the 3+-ONH$_2$ group to a 3'-OH group. Once converted, enzymatic extension can proceed. Further, although U.S. Pat. Nos. 7,544,792 and 8,212,020 did not provide a useful reagent for cleaving the nitrogen-oxygen bond in the 3'-O—NH$_2$ unit in an oligonucleotide to generate an extendable 3'-OH group, U.S. Pat. No. 8,034,923 did. U.S. Pat. No. 8,034,923 taught that the nitrogen-oxygen bond in the 3'-O—NH$_2$ unit could be cleaved by an aqueous solution of sodium nitrite, preferably if buffered to a pH of near six. The product of that cleavage was a 3'-OH group.

However, triphosphates carrying 3'-O—NH$_2$ groups would have additional value if they could be presented in compositions that are substantially free of a triphosphate that carried a 3'-OH group. Here, "substantially free" requires that the triphosphates carrying the 3'-O—NH$_2$ groups contain less than 0.5 mole percent of the triphosphate with a free 3'-OH group, and preferably less than 0.05 mole percent, relative to the triphosphate that has a 3'-O—NH$_2$ group. Such compositions could be used to sequence DNA using a cyclic reversible termination architecture. Such sequencing has substantial utility.

While U.S. Pat. No. 8,034,923 provided an enabling synthesis of nucleoside triphosphates carrying 3'-O—NH$_2$ groups, as well as those triphosphates whose nucleobases carried a linking group appended to a functional group that could be reacted with a tag, that synthesis of the product triphosphate was expensive, requiring purification by high performance liquid chromatography (HPLC). Further, should the nucleoside triphosphate have a linking group (including cleavable linking moieties) attached to the nucleobase and, still further, a tagging moiety (e.g. a fluorescent tag) attached to the linking group, subsequence HPLC is also required, making the synthesis more expensive.

The process for synthesizing such triphosphates disclosed in U.S. Pat. No. 8,034,923 managed the many unstable and cross-reacting groups in the molecule, including the 3'-aminoxy, moiety, the triphosphate moiety, the nucleobase moiety, the linker moiety, and the tagging moiety. As with many triphosphate syntheses, the triphosphate moiety is preferably added in the last step, or in the next-to-last step, in a multistep synthesis to yield triphosphate analogs. Further, with triphosphate analogs that also carry linker chains appended to the nucleobases, the linker can be added earlier, but the fluorescent groups and other tags are generally introduced late in the synthesis, and generally must be introduced when the 3'-ONH$_2$ group is protected. U.S. Pat.

No. 8,034,923 taught that the 3'-$ONH_2$ group be protected as an oxime while the triphosphate is added to the synthetic intermediate. This oxime is then deprotected by treatment with hydroxylamine ($HONH_2$).

Nevertheless, triphosphates carrying a 3'-$ONH_2$ group proved to have disadvantages. One disadvantage arose from the intrinsic reactivity of the 3'-$ONH_2$ moiety itself. The 3'-$ONH_2$ moiety reacts with aldehydes and ketones that might be present to form oximes. For example, acetone reacts with the $ONH_2$ group to form a 3'-ON=$C(CH_3)_2$ oxime. Unfortunately, acetone is abundant in laboratories. A 3'-ON=$C(R_2)$ oxime triphosphate is not easily accepted by many polymerases. Further, it is not efficiently cleaved by buffered sodium nitrite Solutions.

Accordingly, U.S. Pat. No. 8,034,923 taught that hydroxylamine ($HONH_2$) should also be present in compositions containing triphosphates having a 3'-$ONH_2$ moiety. U.S. Pat. No. 8,034,923 taught that having hydroxylamine to compositions containing the triphosphates would scavenge adventitious aldehydes, or reversibly cleave the oximes should they be formed.

Unfortunately, these nucleoside triphosphate analogs having a 3'-$ONH_2$ moiety were found to decompose upon storage to generate triphosphates carrying a 3'-OH moiety.

BRIEF SUMMARY OF THE INVENTION

This invention is based on the discovery of a mechanism for the undesired decomposition of the 3'-$ONH_2$ unit to generate a triphosphate, carrying a 3'-OH moiety. While not wishing to be bound by theory, the conversion of the 3'-nucleoside-O—$NH_2$ group to a 3'-nucleoside-OH appears to arise from the presence of hydroxylamine, the same hydroxylamine that is taught in the art to be used in a final step of triphosphate synthesis, and taught in the art to be necessary to prevent the 3'-nucleoside-O—$NH_2$ from reacting with aldehydes and ketones to form oximes in the triphosphate compositions. This invention covers aqueous compositions of triphosphates that lack hydroxylamine. Further, this invention covers aqueous compositions of triphosphates that contain an alkoxylamine, preferably methoxylamine. Further this invention covers process for synthesizing such compositions, where the triphosphate is released from the support using an alkoxylamine, preferably methoxylamine.

BRIEF DESCRIPTION OF THE SEVERAL VIEWS OF THE DRAWING(S)

FIG. 1. Schematic showing the procedure of the instant invention for the synthesis of nucleoside triphosphate analogs having a 3'-$ONH_2$ moiety.

Figure 2:
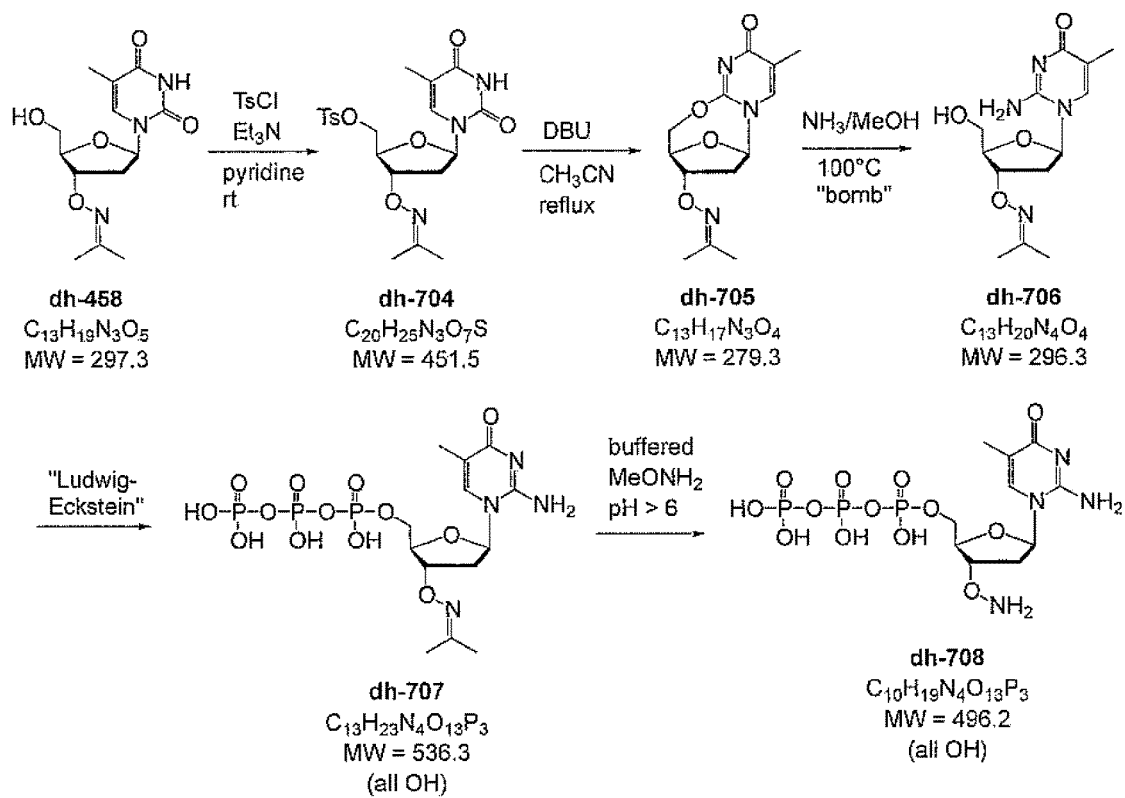

FIG. 2. Schematic showing the procedure of the instant invention for the synthesis of nucleoside triphosphate analogs having a 3'-$ONH_2$ moiety, where the nucleobase is not a standard nucleobase.

Figure 3:
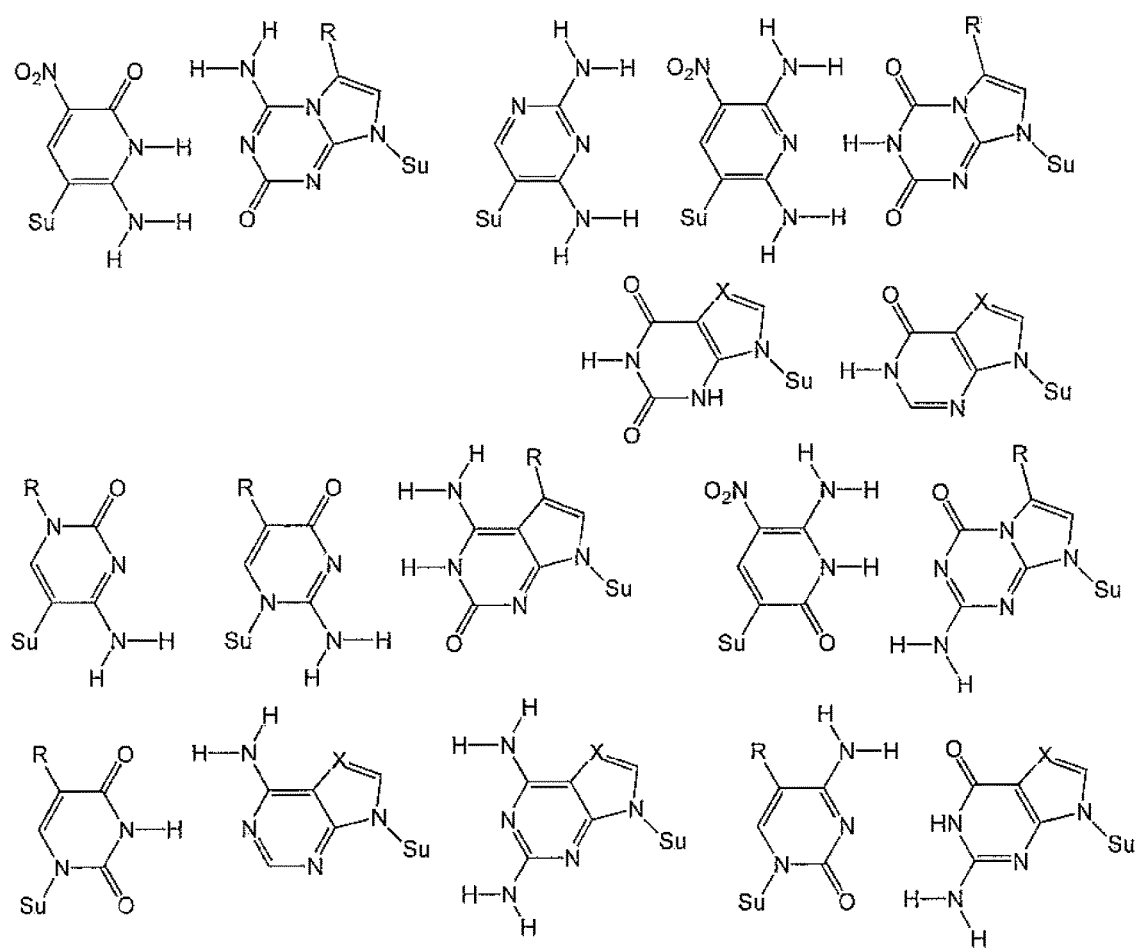

FIG. 3. By shuffling hydrogen bonding groups with a Watson-Crick geometry, a total of 6 nucleobase pairs are possible, having both size and hydrogen bonding complementarity. Different heterocyclic ring systems attached differently to the sugar implement various of these hydrogen bonding patterns. Oligonucleotides containing these non-standard nucleotides also need to be sequenced. Therefore, 3'-$ONH_2$ moieties are also valuable.

Figure 4:
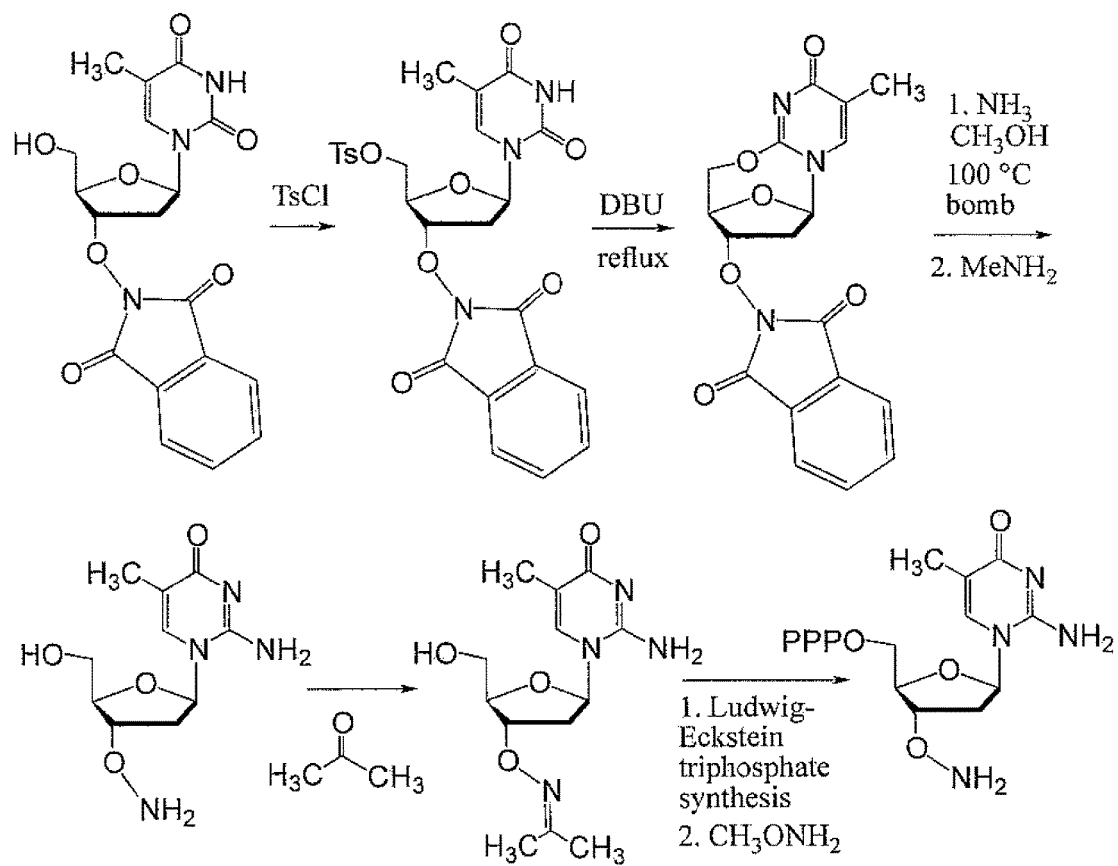

FIG. 4. Synthesis of a non-standard triphosphate carrying a 3'$ONH_2$ moiety by the Ludwig-Eckstein procedure, but in solution.

DETAILED DESCRIPTION OF THE INVENTION

The discovery that the triphosphates disclosed in U.S. Pat. No. 8,034,923 carrying the 3'-$ONH_2$ moiety decompose, upon storage for times longer than one week, to give contaminating triphosphates having a standard, and extendable, 3'-OH group, creates the need for the instant invention. This invention is based on the discovery that the undesired decomposition of the 3'-$ONH_2$ moiety to generate a 3'-OH moiety arose from the presence of hydroxylamine. This is the same hydroxylamine that is taught in the art to be used in a final step of triphosphate synthesis and that is taught to be present in useful compositions of triphosphates. Without wishing to be bound by theory, the H—$ONH_2$ molecule may react with dioxygen or other oxidizing species to give a radical, and this radical species cleaves the RO—$NH_2$ bond to generate an R—OH species.

The consequent invention is a composition that comprises nucleoside, nucleoside triphosphate, nucleotide or oligonucleotide species that have a 3'-$ONH_2$ moiety in an aqueous mixture that is substantially free of hydroxylamine. "Substantially" in this context means less than 1 micromolar, more preferably less than 1 nanomolar. As an additional inventive feature, these aqueous mixtures comprise a molecular species, again not the hydroxylamine taught in the art, that prevents the RO—$NH_2$ moiety from reacting with adventitious aldehydes and ketones to give oximes. Further, this discovery requires a new process to synthesize this composition, a process that does not use hydroxylamine in any step after the triphosphate is synthesized. In particular, the process it limited by not using hydroxylamine to free the RO—$NH_2$ moiety from its protection during triphosphate.

First, the instant invention replaces hydroxylamine wherever it is used by an alkoxylamine. The presently preferred alkoxylamine is methoxylamine ($H_3C$—O—$NH_2$).

For a synthetic route to yield compositions containing nucleoside-O—$NH_2$ triphosphates, both without a linker and, optionally with a linker and, optionally, with a tag attached to a functional group on the linker, in a stable form led to the invention of a process that also reduces the cost of synthesis of these species. Here, the carbonyl species (aldehyde or ketone) that protects the RO—$NH_2$ moiety during the synthesis of the triphosphate and, optionally the attachment of a tagging moiety (e.g. a fluorescent moiety) to a linker side chain, is not free in solution. Rather, the nucleoside derivative having a free 5'-OH group is immobilized on a solid support by way its RO—$NH_2$ moiety through its formation of an oxime with a carbonyl moiety that is attached to the solid support. This allows the triphosphate moiety to be added to the 5'-OH group of an immobilized nucleoside derivative having the schematic formula 5'-HO-nucleoside-3'-O—N=C—support. Once the triphosphate is synthesized, the excess reagents and biproducts are washed from the support. Then, the triphosphate is released from the support by a transoximation reaction using an alkoxylamine, preferably methoxylamine, not hydroxylamine.

The presently preferred immobilized aldehyde is Tenta-Gel aldehyde resin (Rapp Polymere, Germany). The presently preferred alkoxylamine is methoxylamine. The presently preferred procedure for adding the triphosphate moiety to the 5'-hydroxyl group of the immobilized nucleoside derivative is provided by [Ludwig, J., Eckstein, F. (1989) Rapid and efficient synthesis of nucleoside 5'-O-(1-thio-triphosphates), 5'-triphosphates and 2',3'-cyclophosphorothioates using 2-chloro-4h-1,3,2-benzodioxaphosphorin-4-one. *J. Org. Chem.* 54, 631-635]. The presently preferred composition of matter comprises a triphosphate carrying a 3'-O—NH$_2$ moiety in aqueous solution where the concentration of hydroxylamine is less than 0.0001 molar. The presently preferred composition contains less than 0.5 mole percent of the analogous triphosphate with a free 3'-OH group, more preferably less than 0.05 mole percent, and most preferably less than 0.005 mole percent, calculated relative to the triphosphate carrying a 3'-O—NH$_2$ moiety.

As is well known in the art, the Ludwig-Eckstein synthesis can also produce thiol triphosphates, if sulfur is used as the oxidant. Thus, the procedure provided here also is a procedure to produce the analogous thiotriphosphates.

This disclosure also covers nucleoside triphosphates carrying a 3'-O—NH$_2$ moiety, but where the nucleobase is nonstandard, as disclosed in U.S. Pat. Nos. 5,432,272, 6,001,983, 6,037,120, 6,140,496, 6,617,106, 7,741,294, 8,389,703, 8,614,072, 8,354,225, and 9,062,345. Non-standard nucleobases also form pairs following the two Watson-Crick complementary rules (size complementarity and hydrogen bond complementarity), but with rearrange hydrogen bonding patterns.

As known in the art, hydrogen-bonding patterns are distinct in concept from the heterocycle used to implement the hydrogen-bonding patterns. Thus, guanosine implements the puADD hydrogen-bonding pattern. So does, however, 7-deazaguanosine, 3-deazaguanosine, and 3,7-dideazaguanosine, and heterocycles that carry side chains to which are appended functional groups, such as fluorescent, fluorescent quencher, attachment, or metal complexing groups.

As non-standard nucleotides become more widely used, especially in in vitro laboratory evolution procedures, as described in U.S. Pat. No. 8,586,303, procedures to sequence oligonucleotides containing them become necessary. These can be implemented using nonstandard nucleoside triphosphates carrying 3'-ONH$_2$ units.

This procedure used TentaGel aldehyde resin (Rapp Polymere, Germany) as a solid support for the Ludwig-Eckstein triphosphate synthesis procedure. The starting material is a nucleoside with a free 5'-OH group and a 3'-ONH$_2$ moiety. That nucleoside may have a nucleobase that carries a side chain, preferably attached to the 5-position of the pyrimidine, or the analogous position on another six-ring heterocycle, or to the 7-position of a 7-deazapurine. That side chain can be cleavable, containing a disulfide moiety as known in the art, or a diol that is cleavable using periodate. These are disclosed as well in U.S. Pat. Nos. 7,544,794, 8,034,923, and 8,212,020, which are hereby incorporated by reference in their entirety into this disclosure.

The linker attached to the nucleobase is preferably —CC—(CH$_2$)$_n$—NH-substituent, wherein 12 is preferably 1 or 2, and said substituent preferably carries a cleavable moiety. The cleavability is most preferably a disulfide moiety or a 1,2-diol moiety. Linkers are disclosed in U.S. Pat. Nos. 7,544,794, 8,034,923, and 8,212,020, as well as in US Patent Application 20160355541 and art cited therein. These are hereby incorporated by reference in their entirety into this disclosure.

The nucleoside having a free 5'-OH group and a 3'-ONH$_2$ moiety and, optionally, a linker attached to a nucleobase, is contacted to the TentaGel aldehyde resin an aqueous mixture, where it reacts to form an oxime that covalently attaches the nucleoside derivative to that support.

The Ludwig-Eckstein procedure is then applied to supports carrying the nucleoside derivative. In the first step, 2-chloro-4H-1,3,2-benzodioxaphosphorin-4-one is contacted with the support, reacting with the free 5'-OH group; during this procedure. Here, the 3'-ONH$_2$ moiety is unreactive because it exists as an oxime. This is reacted with a salt of pyrophosphate to yield a cyclic triphosphate with one of the phosphorus atoms in the +3 oxidation state. The intermediate is then oxidized with an oxidizant such as iodine or sulfur to yield the O and S triphosphates derivatives respectively. These triphosphate products are still attached to the solid support.

The product triphosphate is released from the support by elution with an aqueous solution of an alkoxylamine, preferentially methoxylamine. After preferably 90 minutes, the eluate contained the desired triphosphate as the main component of the total nucleotide material. No side products that have a 3'-OH moiety are present.

EXAMPLES

Example 1

Thymidine Derivatives

A. Loading of the Nucleoside onto the Resin.

TentaGel-CHO HL-form (1.0 g, carrying 0.47 mmol of aldehyde carbonyl) was weighed into a peptide synthesis vessel ("PSV", not silanized, 25 mL volume) and pre-swollen overnight in toluene (20 mL) with shaking at room temperature. After 18 h, the solvents were removed, and the support was washed several times with toluene, dichloromethane (DCM) and methanol (MeOH) (3×20 mL each solvent), and then with then water (20 mL). The resin was then swollen in aqueous NaOAc buffer (50 mM, pH 5, 20 mL) and drained.

Separately, crude thymidine with a free underivatized 3'-OH group (lyophilized) was dissolved in NaOAc buffer (50 mM, pH 5, 20 mL), microfiltered (0.45 μm; only little insoluble material was seen) and added to the resin. The vessel containing both the resin and the thymidine derivative was shaken at room temperature.

The progress of the reaction was followed by UV measurement of the aqueous solution. After time intervals, shaking was stopped, aliquots (50 μL) of the supernatant were removed and diluted with water (950 μL), and the UV absorbance was measured (nanodrop, 260 nm). In cases where this was done, the loading reaches a plateau after 2 days. The overall loading was calculated from the remaining nucleoside in solution:

$$t=0\ A_{260}=8.2\ \text{AU}\ t=44\ h\ 1.2\ \text{AU}$$

After 44 h, the solution was drained and the resin was washed with water (6×20 mL, 30 min shaking each time), followed by MeOH (3×20 mL). The resin was about equally distributed into two flasks (A and B) and coevaporated with pyridine (2×20 mL each), followed by toluene (2×20 mL each), and dried at HV for several days.

According to the UV measurements, total loading was about 7.0 AU, as measured in 50 μL diluted with 950 μL of water (20× dil). With total solution=20 mL and extinction coefficient=8800, this gives a total loading of 20×20×7.0/8800=0.32 mmol on 1 g of resin. This number is reproducible for a batch of resin.

B. Preparation of Triethylammonium Pyrophosphate Solution in Acetonitrile.

Dowex 50W X8 ion exchange resin (50-100 mesh, 25 g) was weighed into a 50 mL Falcon tube, briefly washed with water (3×20 mL) and transferred into an FLC column, where it was again washed (ca. 1-2 drops per second) with water (200 mL), followed by aqueous HCl solution (1 M, 100 mL)

and water again (100 mL, when pH of eluate was neutral). Sodium pyrophosphate (2.7 g, 10 mmol) was dissolved in water (60 mL) at room temperature and loaded onto the column (eluting begins during the loading). The hydrogen form was eluted with water into an ice-cold solution of triethylamine (2.8 mL, 20 mmol) in EtOH (40 mL) until the pH of the elute was 5 (ca. 100 mL). The solution was concentrated in vacuo (rotavap, bath temperature 33° C.). The resulting oil was coevaporated from EtOH (2×80 mL) to remove all water, resulting in a colorless oil. Addition of DMF (50 mL) led to the precipitation of a colorless solid.

The mixture was evaporated in vacuo (rotary evaporation, bath temperature 33° C., then high vacuum) to remove all EtOH and DMF. The resulting solids were completely redissolved in acetonitrile (90 mL) upon gentle heating to ca. 40° C. The solution was cooled to room temperature, molecular sieves (3 Å, freshly activated) were added, and the flask was stored at 4° C. Storage of this stock solution in anhydrous acetonitrile at 4° C. for several days led to some precipitate being formed, perhaps (excess pyrophosphate salt).

The clear supernatant was analyzed/quantified as follows: An aliquot (300 µL) of the supernatant was mixed with $D_2O$ (200 µL) and analyzed by $^{31}$P-NMR, showing pure pyrophosphate. Addition of aqueous $KH_2PO_4$ (1 M, 60 µL) gave an additional peak; integration of the two peaks gave '100' for the monophosphate peak and '25' for the pyrophosphate peak; therefore, the concentration of the pyrophosphate stock solution in acetonitrile is 25 mM (an equal peak would be 100 mM, for 2 P-equivalents).

C. Triphosphate Synthesis (Ludwig-Eckstein) with Triethylammonium Pyrophosphate.

All solvents for water-sensitive reactions had been dried over molecular sieves (3 Å) for several days. To reduce potential hydrolysis, the screw cap was lined with two (not just one) silicon/PTFE disks. The resin ("saturated" loading, 220 mg, 0.07 mmol 5'-OH) was weighed into an oven-dried 10 mL peptide synthesis vessel (PSV), and the vessel was capped with a screw-cap containing a hole to allow perforation of the underlying silicon/PTFE disks with syringe needles without the need to ever remove the cap. The resin was swollen in pyridine (2×10 mL) and drained. Pyridine (2 mL), DMF (1 mL) and dioxane (2 mL) were added. A stock solution of the chlorophosphite in dioxane was prepared by dissolving 230 mg of chlorophosphite in 4.6 mL of dioxane (analysis by NMR ($^{31}$P, $CDCl_3$) showed it to contain 90% P—Cl). An aliquot (2.2 mL, 0.5 mmol P—Cl, ~8 eq) of this stock solution was added to the swollen resin. The vessel was shaken at room temperature for 4 min, then drained. The resin was immediately treated with a mixture of $P_2O_7.HNEt_3$-solution (25 mM in $CH_3CN$, 8 mL, 0.2 mmol, ~3 eq) and triethylamine (70 µL, 0.5 mmol). The vessel was shaken at room temperature for 30 min (shorter reaction times led to incomplete reaction), then drained. A solution of iodine (67 mg, 0.25 mmol) in pyridine (10 mL) containing water (200 µL) was added at once. The vessel was shaken at room temperature for 30 min, and the solution was drained. The resin was washed with pyridine (2×10 mL) containing water (0.2 mL each) to remove any remaining iodine, then with repeated washes (shaking ca. 15 min each) of pyridine/ $H_2O$ (1:1, 10 mL), $H_2O$ (10 mL), pyridine/$H_2O$ (1:1, 10 mL), and finally $H_2O$ (2×10 mL). The resin was briefly washed with MeOH (HPLC, 2×10 mL) for easier transfer, dried under nitrogen flow for 2 min, and then about equally distributed into 3 eppendorf tubes with screw caps. The resins were washed with aqueous Tris buffer (10 mM, pH 8, 4×1.4 mL each, for 30 min each) with shaking in the tube holding insert on the vortexer at low speed. After each washing, the tube were centrifuged (2 min @ 13,000 rpm) and the supernatants were decanted (discarded). The tubes with the drained resins were then stored at −20° C.

D. Elution of the Triphosphate with Buffered Methoxylamine Solution.

The buffered $MeONH_2$ solution was prepared by diluting $MeONH_2.HCl$ (25-30% in water, 80 µL, ca. 0.3 mmol) with water (HPLC, 1.25 mL), neutralizing with aqueous NaOH solution (10 M, 25 µL, 0.25 mmol), and buffering with aqueous sodium acetate buffer (1 M, pH 5.5, 160 µL, 0.16 mmol). One tube containing drained resin (ca. 20 µmol oxime) was warmed to room temperature, treated with buffered $MeONH_2$ solution (1 mL) and shaken at room temperature in the tube holding insert on the vortexer with low speed shaking. After time intervals (90 min, 6 h), the tube was centrifuged (2 min @ 13,000 rpm). An aliquot (20 µL) of the supernatant was diluted with water (380 µL), and the UV absorbance was measured (nanodrop, 260 nm).

The dilute samples were treated with acetone (HPLC, 1 µL) to form the acetoximes for better analysis. These oxime samples were analyzed by ion-exchange HPLC (ammonium bicarbonate gradient). Their chromatograms indicated that the composition contained 77% of triphosphate after 2 h of elution, and still 73% after 6 h, when some side products from less accessible sites on the resin started to increase. The most prevalent side products were the peaks eluting after the triphosphate, presumably produced by "over-phosphorylation", tallying a combined 12%, as well as diphosphate and hydrolyzed monophosphite ("rp-D"), each about 3-6%. None of these contained a free 3'-OH group.

Example 2

Methylisocytidine Derivatives

Synthesis of disoMeCTP-$ONH_2$ was prepared by aminolysis of 2,5'-anhydro-T-$ONH_2$ (preferably as the ON-phthalimide), followed by triphosphate synthesis, analogous to the procedure published by [Jurczyk et al. (1998) Helv. Chim. Acta 81, 793-811]. (FIG. 4)

The triphosphate oxime dh-707 was prepared by the procedure from Jurczyk et al., with some minor modifications. Since this nucleoside analog is acid sensitive (depyrimidinylation at acidic pH, at least at pH<5; stable at pH 6 or higher), the common protocol for the $MeONH_2$ cleavage of the oxime (usually carried out at pH 5.5) to the ready-to-use aminoxy terminator dh-708 was adjusted to run at slightly higher pH.

What is claimed is:

1. A composition comprising an aqueous solution containing an alkoxylamine, hydroxylamine at a concentration of less than 1 micromolar and a molecule having the structure:

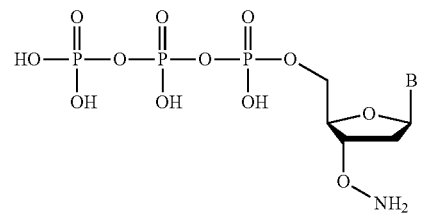

or one of its ionized forms, wherein B is a heterocycle selected from the group consisting of

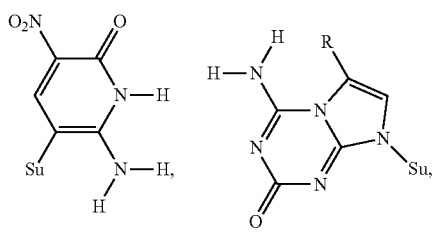
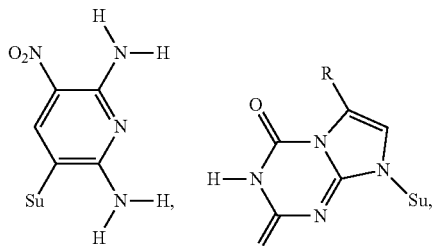
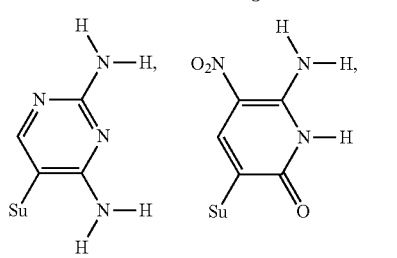
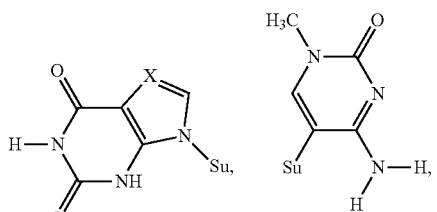
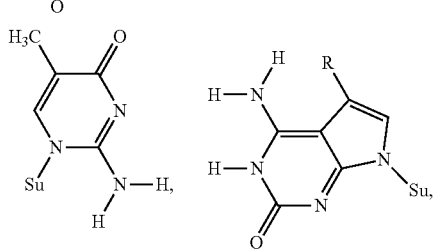
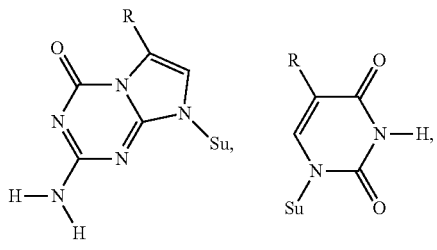
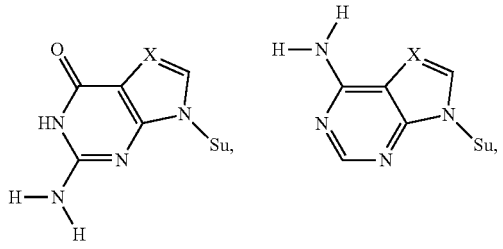

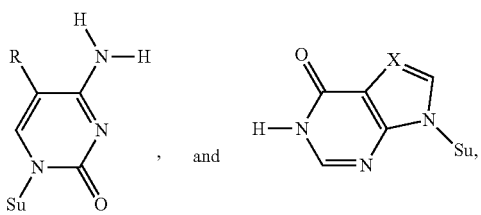

, and wherein Su indicates the point of attachment of the heterocycle to the sugar, R is either H, CH$_3$, or a functionalized side chain, and X is either N or C—R.

2. The composition of claim 1, wherein said alkoxylamine is methoxylamine.

3. The composition of claim 1, wherein said heterocycle B is selected from the group consisting of thymine, uracil, cytosine, guanine, adenine, 7-deazaadenine, 7-deazaguanine, and isocytosine and the alkoxylamine is methoxylamine.

4. The composition of claim 1, wherein said heterocycle B is selected from the group consisting of thymine and isocytosine and the alkoxylamine is methoxylamine.

5. The composition of claim 1, wherein appended to heterocycle B is a linker that comprises either a disulfide moiety or a 1,2-diol moiety and the alkoxylamine is methoxylamine.

6. A process for preparing a compound of having the structure:

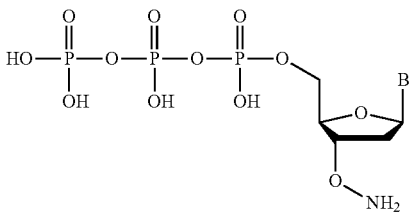

or one of its ionized forms, wherein B is a heterocycle selected from the group consisting of

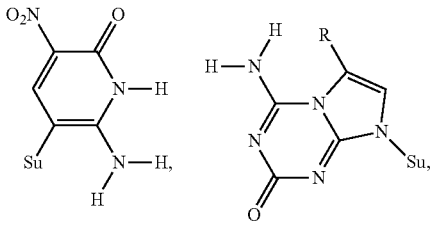
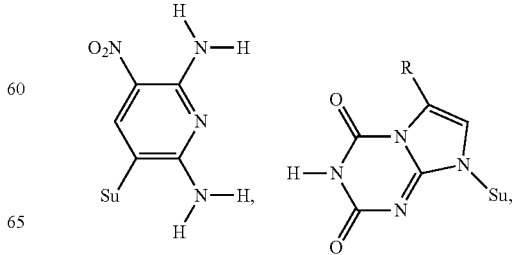

-continued

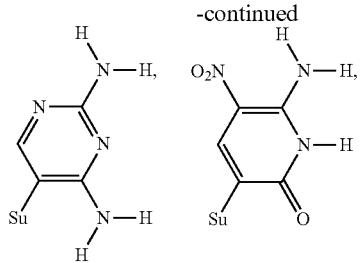
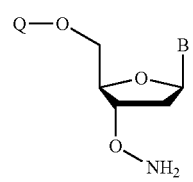
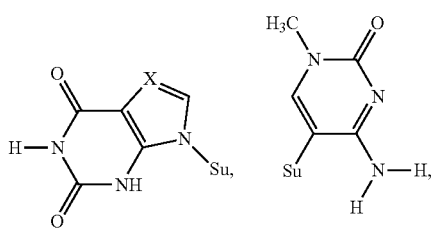
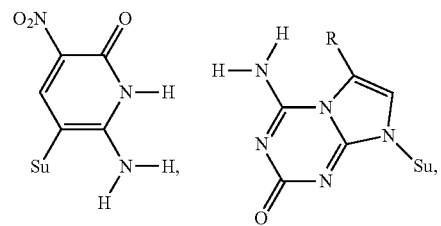
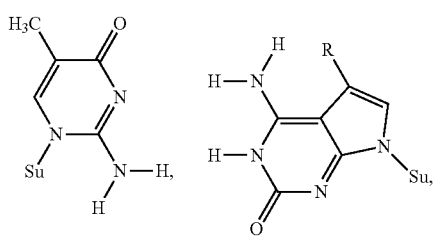
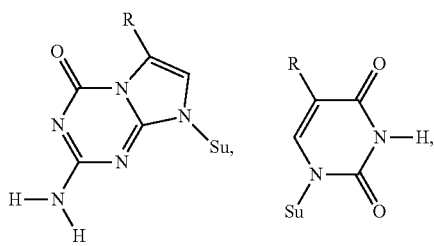
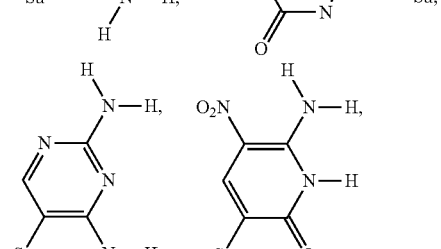
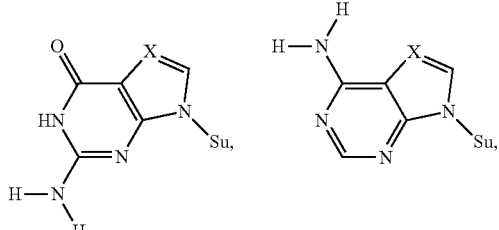
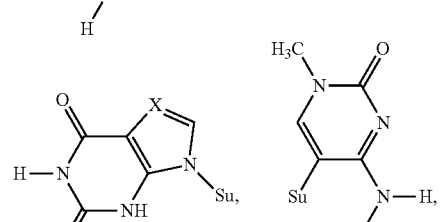
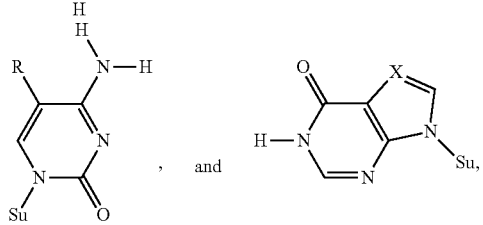, and
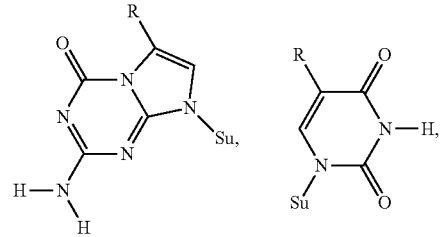

wherein Su indicates the point of attachment of the heterocycle to the sugar, R is H, CH₃, or a functionalized side chain, and X is either N or C—R, wherein said process comprises:

(a) contacting a solid phase having an immobilized aldehyde or ketone moiety with compound having the following structure wherein Q is either H or a dimethoxytrityl group, and B is a heterocycle selected from the group consisting of -continued

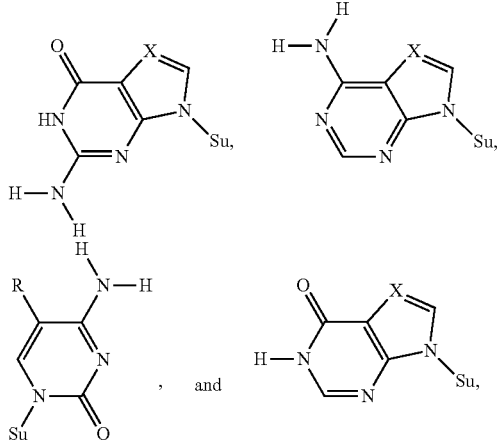

wherein Su indicates the point of attachment of the heterocycle to the sugar, R is H, CH$_3$, or a functionalized side chain, and X is either N or C—R, followed by (b) contacting the composition from step (a) with 2-chloro-4H-1,3,2-benzodioxaphosphorin-4-one, followed by (c) contacting the composition from step (b) with an ammonium salt of a pyrophosphate, followed by (d) oxidizing the composition from step (c), followed by (e) washing the composition from step (d) with an aqueous solution comprising an alkoxylamine.

7. The process of claim 6, wherein appended to heterocycle B is a linker that comprises either a disulfide moiety or a 1,2-diol moiety.

8. The process of claim 6, wherein said heterocycle B is selected from the group consisting of thymine, uracil, cytosine, guanine, adenine, 7-deazaadenine, 7-deazaguanine, and isocytosine.

9. The process of claim 6, wherein said heterocycle B is selected from the group consisting of thymine and isocytosine.

10. The process of claim 6, wherein the alkoxylamine is methoxylamine.

11. The composition of claim 1, wherein said solution contains less than 1 nanomolar hydroxylamine.

12. The composition of claim 1, wherein the composition contains less than 0.5 mole percent of the molecule having the structure with a 3'-OH group relative to the molecule having the structure with a 3'-O—NH$_2$ group.

13. The composition of claim 1, wherein the composition contains less than 0.05 mole percent of the molecule having the structure with a 3'-OH group relative to the molecule having the structure with a 3'-O—NH$_2$ group.

14. The process of claim 6, comprising in step e) washing the composition from step (d) with the aqueous solution comprising the alkoxylamine, wherein the aqueous solution does not contain hydroxylamine.

15. The process of claim 6, wherein the process does not comprise using hydroxylamine in any step after step d).

* * * * *

UNITED STATES PATENT AND TRADEMARK OFFICE
CERTIFICATE OF CORRECTION

PATENT NO.        : 10,472,383 B2
APPLICATION NO.   : 15/460475
DATED             : November 12, 2019
INVENTOR(S)       : Steven A. Benner Page 1 of 1

It is certified that error appears in the above-identified patent and that said Letters Patent is hereby corrected as shown below:

In the Specification

Column 3,
Line 14, "nitrite Solutions." should read --nitrite solutions.--.

Column 5,
Line 51, "wherein 12" should read --wherein $n$--.

Column 7,
Line 7, "was 5" should read --was ~ 5--.

Signed and Sealed this
Sixteenth Day of June, 2020

Andrei Iancu
*Director of the United States Patent and Trademark Office*